United States Patent [19]

Laghi

[11] Patent Number: 5,507,837
[45] Date of Patent: Apr. 16, 1996

[54] PROSTHETIC LOCKING DEVICE WITH INTEGRAL PYRAMID

[76] Inventor: Aldo A. Laghi, 2400 Feathersound Dr., Apt. #1118, Clearwater, Fla. 34622

[21] Appl. No.: 310,129

[22] Filed: Sep. 21, 1994

[51] Int. Cl.⁶ .................................. A61F 2/62; A61F 2/80
[52] U.S. Cl. .................................. 623/38; 623/33; 264/274
[58] Field of Search ..................... 623/38, 55, 53, 623/33, 47–52; 403/87, 362; 264/274

[56] References Cited

U.S. PATENT DOCUMENTS

| | | | |
|---|---|---|---|
| 1,576,874 | 3/1926 | Stevens | 264/274 X |
| 2,972,655 | 2/1961 | Strauss | 264/274 X |
| 3,659,294 | 5/1972 | Glabiszewski | 623/38 |
| 4,608,054 | 8/1986 | Schröder | 623/39 |
| 5,158,570 | 10/1992 | Schey et al. | 623/52 |
| 5,163,965 | 11/1992 | Rasmusson et al. | 623/36 |
| 5,201,774 | 4/1993 | Greene | 623/34 |
| 5,226,918 | 7/1993 | Silagy et al. | 623/32 |
| 5,376,129 | 12/1994 | Faulkner et al. | 623/33 |

*Primary Examiner*—David H. Willse
*Attorney, Agent, or Firm*—Joseph C. Mason, Jr.; Ronald E. Smith

[57] ABSTRACT

A light-in-weight locking device laminated within a hard prosthesis socket includes a plastic base molded in gripping relation to a metallic pyramid so that the locking device is a one piece, integrally formed unit. A flange of the pyramid is embedded within the base to prevent separation of the base and pyramid. One or more recesses are formed in a central part of the pyramid and plastic positioned in those recesses prevents relative rotation between the base and the pyramid. Circumferentially extending cavities formed in the base receive parts of the prosthesis socket to prevent relative rotation between the base and the socket. The unit has a truncate longitudinal extent so that it easily fits within the socket.

5 Claims, 2 Drawing Sheets

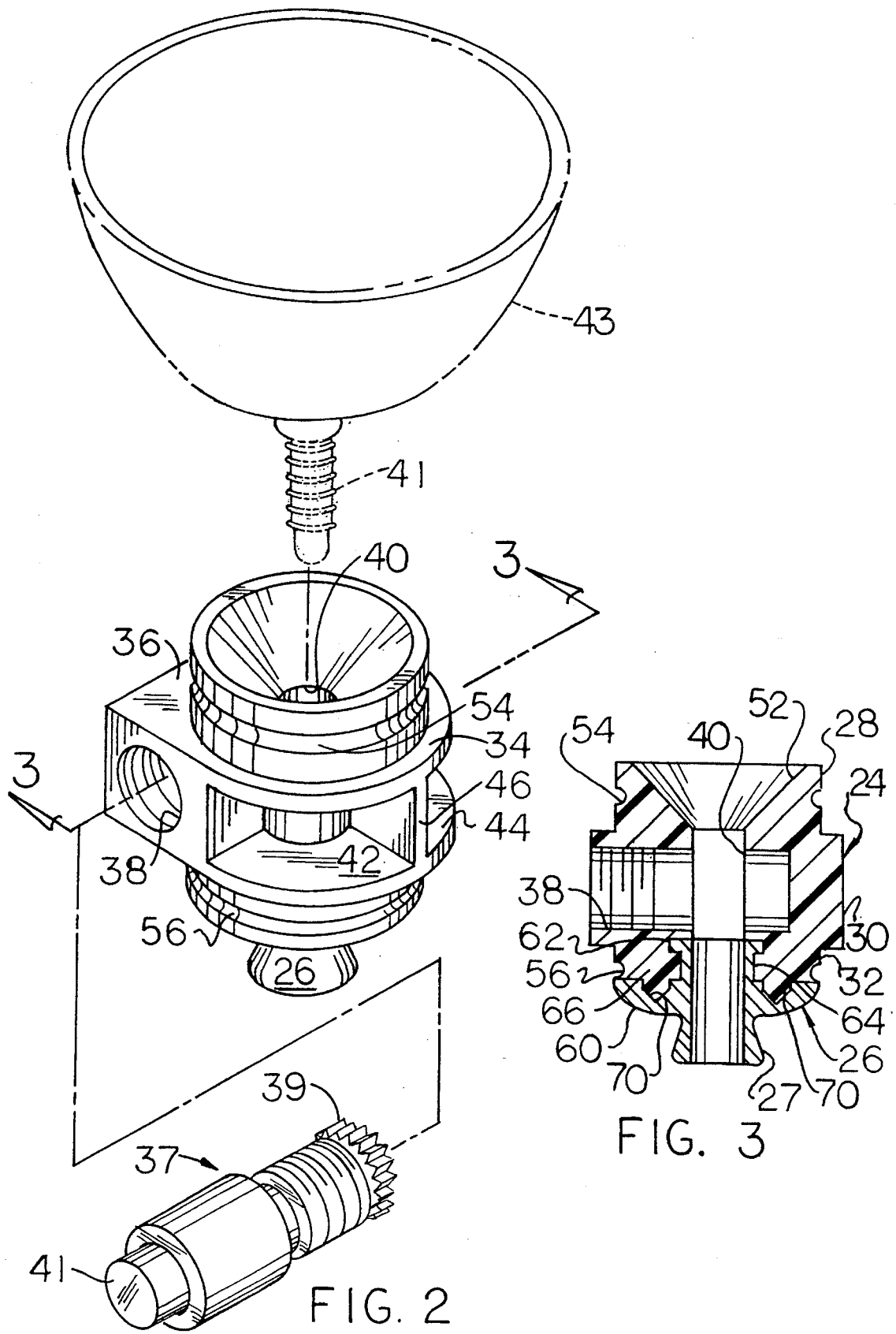

PROSTHETIC LOCKING DEVICE WITH INTEGRAL PYRAMID

BACKGROUND OF THE INVENTION

1. Field of the Invention

This invention relates, generally, to the art of prosthetics. More particularly, it relates to a locking device that is laminated within the hard socket of a prosthetic limb.

2. Description of the Prior Art

The residual limb or stump of an amputee is typically placed into a cushioned liner having an open proximal end for receiving the stump and a closed distal end to which is attached a metallic locking pin that extends therefrom along the longitudinal axis of the liner.

The liner may be formed of any suitable material, although the present inventor has recently introduced a unique liner made of transparent silicone that includes a novel means for interlocking the metallic locking pin to said silicone liner.

The stump, protected by the liner, is inserted into the hard socket of a prosthetic limb, and the locking pin extending from the distal end of the liner engages a locking device which is laminated into said hard socket. The locking device secures the pin and hence the liner to the prosthesis; unlocking means are included as a part of the locking device so that the amputee may remove the prosthesis when desired.

The locking device is in turn attached to an adapter plate which attaches to an alignment pyramid. Thus, the art teaches that three pieces are needed to connect the liner to the prosthetic device, i.e., the locking device, the adapter plate, and the alignment pyramid.

There are several drawbacks of the known three piece design. For example, the three pieces are heavy, expensive to manufacture, and have a substantial length or height when assembled together to form the locking means. Such length prevents the locking means from being used in prosthetic sockets that lack sufficient space to accommodate such lengths.

The earlier device also tends to rotate with respect to the prosthetic socket within which it is embedded.

What is needed, then, is an improved locking device. An improved device would have fewer parts so that it would be less expensive to manufacture, would weigh less so that it would place less burden on its user, would have a truncate extent relative to the elongate extent of the known devices so that it could be used even with sockets having limited space for the accommodation of locking devices, and would not rotate with respect to the prosthesis so that it would not require frequent adjustment or repair.

However, in view of the prior art at the time the present invention was made, it was not obvious to those of ordinary skill in this art how an improved device could be provided.

SUMMARY OF THE INVENTION

The longstanding but heretofore unfulfilled need for an improved locking device is now met by a novel locking means having an adapter plate, locking device, and alignment pyramid provided as a single unit. The one-piece device is less expensive to manufacture, weighs less, has a more truncate extent, and is less prone to rotation than its prior art counterparts.

The novel device includes a metal pyramid integrally molded within a base member of high strength plastic. Interlocking means are provided to prevent relative rotation between the metal pyramid and the plastic base and to provide rigidity. Moreover, the plastic base is specifically configured to prevent relative rotation between it and the prosthetic socket within which it is embedded, and the pyramid is specifically configured to prevent its retration from the plastic base.

The pyramid member includes a pyramid-shaped main part, a flange that is longitudinally spaced apart from the main part, and a neck that interconnects the main part and the flange. The neck has a diameter less than the respective diameters of the main part and the flange so that the plastic that forms the base member is positioned around the neck and between the flange and the main part of the pyramid member to retain the pyramid member within the base member.

The plastic base member includes a first end of cylindrical construction, said first end having a first diameter, a central part having a breadth greater than said first diameter, and a second end of cylindrical construction having a diameter substantially equal to said first diameter. This construction eliminates the need for a separate adapter plate.

A bore is formed in the plastic base member and the metallic pyramid member, said bore being coincident with a longitudinal axis of symmetry of the novel device. The bore has a first funnel-shaped end formed in the first end of the plastic base member and in a contiguous part of the central part, and the bore has a central part formed in the central part of the base member, and has a second end formed in the second end of the base member and in the metallic pyramid member, said central part and said second end of the bore having a diameter equal to the smallest diameter of the first funnel-shaped end of the bore.

Accordingly, the first funnel-shaped end of the bore receives a distal end of a liner, and the central part of the bore and the second part of the bore receive a locking pin that is mounted to said distal end of said liner.

The central part of the plastic base member further includes at least one cavity formed therein, said cavity receiving therewithin a part of a prosthesis socket when the base member is laminated into the socket, said reception preventing relative rotation between the base member and the socket even after the socket has shrunk.

In a preferred embodiment, said at least one cavity includes a pair of circumferentially extending cavities divided from one another by a partition wall, and each cavity of said pair of cavities has a circumferential extent of about ninety degrees.

A plurality of circumferentially spaced apart recesses are formed in a base part of the main part of the pyramid member, so that the plastic that forms the base member is disposed within each recess of said plurality of recesses to prevent relative rotation between the base member and the pyramid member.

It is therefore clear that the primary object of this invention is to advance the art of prosthetic locking devices by providing a one-piece locking device of low weight, low cost, and truncate extent.

Another major object is to provide such a device with anti-rotation means.

These and other important objects, features and advantages of the invention will become apparent as this description proceeds.

The invention accordingly comprises the features of construction, combination of elements and arangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 2 is an exploded perspective view of the novel locking device and the distal end of a liner having a locking pin; and FIG. 3 is a sectional view taken along line 3—3 in FIG. 2.

DETAILED DESCRIPTION OF THE PREFERRED EMBODIMENT

Figure 1:
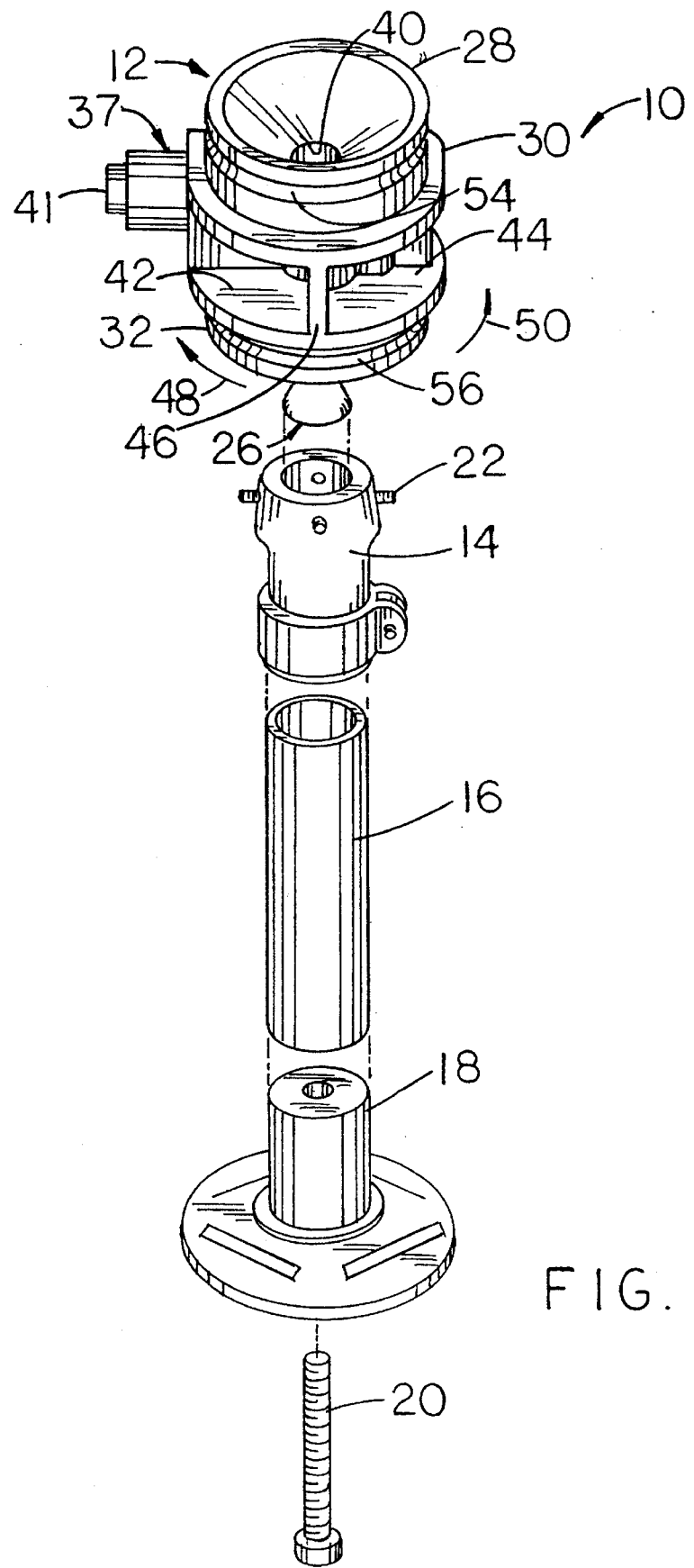
FIG. 1 is an exploded perspective view of an endoskeletal alignment unit including the present invention.

Referring now to FIG. 1, it will there be seen that the environment within which the inventive device is used is denoted as a whole by the reference numeral 10.

Environment 10 is an endoskeletal alignment assembly. It includes novel device 12, a pylon tube clamp 14, a pylon tube 16, a lower pylon tube clamp 18, and a locking bolt 20.

Except for novel device 12, the parts depicted in FIG. 1 are well known. However, it should be understood that a depiction of a typical prior art alignment assembly would include three separate, individual parts in place of novel device 12, i.e., device 12 would be replaced by an adapter plate, a locking device, and a pyramid unit, none of which would be formed integrally with any of the other parts.

Alignment assemblies are needed because the locking pin at the distal end of the liner worn by the amputee is not likely to be positioned in a perfectly vertical alignment when the patient is wearing the prosthesis. Thus, the pyramid member of the prior ark is positioned within pylon tube clamp 14, and set screws 22, of which there are four at equidistantly and circumferentially spaced intervals, are selectively tightened by the prosthetist to ensure that the longitudinal axis of pylon tube 16 is precisely vertical.

Novel device 12 that replaces the three prior art pieces is disclosed in detail in FIGS. 1–3. As perhaps best understood in connection with FIG. 3, novel device 12 includes plastic part 24 and metallic pyramid part 26 formed integrally therewith.

Plastic part 24 includes a first or top part 28 of cylindrical configuration, an integral second or central part 30 having an irregular configuration as perhaps best understood in connection with FIG. 2, and a third or lower part 32 which is also of cylindrical configuration. Note that the diameter of first part 28 is equal to the diameter of third part 32 and that the breadth of second part 30 is greater than that of said first and third parts. The irregular shape of second part 30 includes a circular part 34 (FIG. 2) and a rectangular part 36 that are integrally formed with one another. Part 36 includes a horizontal bore 38 within which is received a locking mechanism 37 that forms no part of the invention per se. Vertical central bore 40, as best understood in connection with FIG. 2, receives locking pin 41 at the distal end of liner 43.

Central bore 40 slightly intersects with bore 38; threads formed on locking pin 41 cause rotation of gear 39 in bore 38 in a first direction when locking pin 41 is inserted into bore 40, said gear forming a part of locking assembly 37, and said gear having teeth that extend slightly into central bore 40. The gear can rotate in one direction only so admission of locking pin 41 into bore 40 is not resisted, but retraction of said pin is prevented since gear 39 will not turn in the opposite direction. Push button 41 is pressed to displace the gear teeth past the locking pin so that the locking pin can be withdrawn to enable the amputee to remove the prosthesis.

It should be understood that plastic base member 24 is embedded within a hard prosthesis socket, not shown. To prevent relative rotation between base member 24 and said socket, a pair of cavities 42, 44 (FIGS. 1 and 2) are formed in central part 30 of base member 24; said cavities are separated by partition wall 46. As indicated by double-headed arcuate arrows 48, 50, each cavity 42 and 44 extends ninety degrees in a circumferential direction.

Both cavities are filled when the hard prosthesis socket, not shown, is formed around plastic base member 24. As the socket cures and shrinks, it will pull away from the bottom of each cavity, but the depth of each cavity is such that some socket material will remain within said cavities even after the socket material has fully cured. Thus, relative rotation between base 24 and said socket, a problem that has long plagued the industry, is prevented.

As best disclosed in FIG. 3, central bore 40 has a funnel-shaped part 52 formed in first part 28 of plastic body 24. Opening 52 at least partially accommodates the complementally formed distal end of prosthesis liner 43 and bore 40 receives pin 41 attached to said liner as aforesaid.

Annular grooves 54 and 56 are formed in first or top part 28 and third or lower part 32, respectively. These grooves are used to tie reinforcing fabric to plastic part 24 before lamination.

Metallic pyramid member 26 is partially embedded within plastic base member 24 as best understood in connection with FIG. 3, i.e., central part 60 thereof has a plastic-contacting side and an exposed side. As mentioned earlier, the sloped, pyramidal sidewalls 27 thereof are engaged by set screws 22 (FIG. 1) for the purpose earlier mentioned. Thus, it should be clear that sidewalls 27 and the spherical surface of central part 60 of pyramid 26 are not embedded within the socket as are the other parts of novel device 12 so that said pyramidal sidewalls may be so engaged.

To retain pyramid 26 to plastic base 24, a retention flange 62 is integrally formed with central part 60 of pyramid 26 through a neck 64 having a diameter less than the respective diameters of the retention flange 62 and said central part 60. Note that pyramidal sidewalls 27 are positioned on a first side of central part 60, and that retention flange 62 is positioned on a second side thereof. When novel device 12 is made (through an injection molding process), flowable plastic surrounds retention flange 62 and neck 64 as at 66, i.e., it enters into the space between said flange 62 and said central part 60. Thus, flange 62 cannot be retracted from said plastic after said plastic has cured.

One or more recesses, collectively denoted 70, are formed in the interior or plastic-contracting side of central part 60; the preferred number of recesses 70 is six, and said recesses 70 are equidistantly and circumferentially spaced from one another. When the flowable plastic is injected into a mold that produces novel device 12, said plastic enters into each recess 70. Thus, when it cures, metallic pyramid 26 cannot rotate relative to plastic body 24.

It should thus be understood that retention flange 62 and recesses 70 cooperate to join together plastic base 24 and metallic pyramid 26. Thus, a single part 12 replaces the three parts heretofore employed. Single part 12 weighs less than the combined weights of the three prior art parts, thereby reducing the load on an amputee having a prosthesis equipped with novel device 12. Moreover, device 12 has less length or height than the collective length of the three prior art parts it replaces, and thus, unlike the three-piece assembly, fits within most hard prosthesis sockets. Device 10 does not rotate with respect to the socket within which it is embedded, and said device 12 costs less to produce than its forerunner, making it more affordable to amputees. Those who work with novel device 12 will note further advantages as well, but the advantages pointed out herein are believed to be the primary advantages.

Base 24 may be made of any high strength plastic such as polycarbonate, epoxy, polyester, polymide, and the like. Metallic pyramid 26 may be made of any suitable metal such as titanium, stainless steel, aluminum, and the like.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

What is claimed is:

1. A prosthetic locking device, comprising:

a base member of plastic construction;

said base member including a locking device for releasably engaging a locking pin at a distal end of a prosthesis liner;

a pyramid member of metallic construction;

said base member being molded onto said pyramid member, said device having a one-piece, integrally formed construction;

said pyramid member including a central part, a pyramid-shaped part formed integrally with said central part on a first, exposed side thereof, a retention flange longitudinally spaced from said central part on a second, plastic-contacting side of said central part, and a neck interconnecting said central part and said retention flange, said neck having a diameter less than a diameter of said retention flange and said central part;

said base member having a first end, a second end, and a central part therebetween;

said first and second ends of said base member having a common diameter and a generally cylindrical configuration, said central part of said base member having a breadth greater than said common diameter;

a bore formed in said base member and in said pyramid member, said bore being coincident with a common longitudinal axis of symmetry of said base member and said pyramid member;

said bore having a first funnel-shaped end formed in said base member first end, a central part formed in said base member central part, and a second end formed in said pyramid member, said central part and second end of said bore having a diameter equal to the smallest diameter of said first funnel-shaped end of said bore;

said first funnel-shaped end of said bore adapted to receive a distal end of a liner;

said central part and said second part of said bore adapted to receive said locking pin; and plastic forming said base member being positioned around said neck and between said retention flange and said central part of said pyramid member to retain said neck and retention flange of said pyramid member within said base member.

2. The device of claim 1, further comprising at least one cavity formed in said central part of said base member, said cavity adapted to receive therewithin a part of a prosthesis socket when said base member is laminated into said socket, said reception preventing relative rotation between said base member and said socket.

3. The device of claim 2, wherein said at least one cavity includes a pair of circumferentially extending cavities divided from one another by a partition wall.

4. The device of claim 3, wherein each cavity of said pair of cavities has a circumferential extent of about ninety degrees.

5. The device of claim 1, further comprising at least one recess formed in a plastic-contacting side of said central part of said pyramid member, said plastic that forms said base member being disposed within said at least one recess to prevent relative rotation between said base member and said pyramid member.

\* \* \* \* \*